United States Patent [19]

Horwell

[11] Patent Number: 4,757,151
[45] Date of Patent: Jul. 12, 1988

[54] 2-SUBSTITUTED-[2-SUBSTITUTED-AMINO]-N-ARYLALKYL-3-[INDOL-3-YL]

[75] Inventor: David C. Horwell, Foxton, England

[73] Assignee: Warner-Lambert Company, Morris Plains, N.J.

[21] Appl. No.: 912,731

[22] Filed: Sep. 30, 1986

Related U.S. Application Data

[63] Continuation-in-part of Ser. No. 798,068, Nov. 14, 1985, abandoned.

[51] Int. Cl.$^4$ ............... C07D 209/04; C07D 405/00; C07D 207/12; C07D 207/273; C07D 207/36; C07D 279/00; C07D 413/00; C07D 401/00
[52] U.S. Cl. .................. 548/469; 548/454; 548/503; 544/3; 544/63; 544/98; 544/106; 544/111; 544/124; 544/145; 544/170; 544/175; 544/224; 544/336; 544/358; 544/360; 544/364; 544/373; 544/405; 544/406; 549/60; 549/62; 546/255; 546/256; 546/261; 546/266; 546/273; 546/275; 546/280; 546/284; 514/19; 514/183; 514/279; 514/299; 514/332; 514/336; 514/337; 514/339; 514/340; 514/342
[58] Field of Search .............. 548/469, 454, 503; 544/3, 63, 98, 106, 111, 124, 145, 170, 175, 224, 336, 358, 360, 364, 373, 405, 406; 546/255, 256, 261, 266, 273, 275, 280, 284; 549/60, 62; 514/19, 183, 279, 299, 332, 336, 337, 339, 340, 342

[56] References Cited

U.S. PATENT DOCUMENTS

| | | | |
|---|---|---|---|
| 3,676,458 | 7/1972 | Kornfeld | 548/495 |
| 3,899,592 | 8/1975 | Suarez et al. | 426/2 |
| 3,965,260 | 6/1976 | McArthur | 514/19 |
| 4,073,795 | 2/1978 | Batcho | 548/497 |
| 4,137,404 | 1/1979 | Batcho et al. | 542/442 |
| 4,140,697 | 2/1979 | Batcho et al. | 548/495 |
| 4,198,501 | 4/1980 | Batcho et al. | 542/443 |
| 4,256,641 | 3/1981 | Batcho et al. | 548/497 |
| 4,285,935 | 8/1981 | Etschenberg et al. | 514/19 |
| 4,316,847 | 2/1982 | Batcho et al. | 548/533 |
| 4,349,543 | 9/1982 | Jacobi et al. | |

FOREIGN PATENT DOCUMENTS 1044142 12/1978 Canada .
6028988 2/1985 Japan .

OTHER PUBLICATIONS

Chemical Abstract 75:141146n Morley et al "Preparation of 2-Pyridyl Esters and Their Use in Peptide Synthesis".
Chemical Abstact 92:140492n Pettit et al "Synthesis of Tryptophan Dipeptides".
Chemical Abstract 98:156723x Uemura et al "Investigation of the Interactions of Peptides in the Assembly of Liposome and Peptide by Fluorescence".
Chemical Abstact 102:96085e Hansem et al "Hexapeptide Amides".
Chemical Abstract 101:38808m Hong et al "Synthesis of a Peptide with Growth Hormone Releasity Activity in Vitro and its Depsipeptide Analog".
Kimura et al "Investigation on the Interactions of Peptides in the Assembly of Liposome and Peptide by Fluorescence" *Biochimica et Biophysica Acta*, 729 (1983) 28–34.
Andersen et al "Clionamide, a Major Metabolite of the Sponge *Cliona celata* Grant, *Can. J. Chem.* vol. 57, 1979, pp. 2325–2328.

*Primary Examiner*—Delbert R. Phillips
*Assistant Examiner*—Nathan M. Nutter
*Attorney, Agent, or Firm*—Jerry F. Janssen

[57] ABSTRACT

Certain 2-substituted-[2-substituted-amino]-N-arylalkyl-3-[indol-3-yl]propanamides demonstrate activity as appetite suppressants. The compounds, pharmaceutical compositions, and a method of suppressing appetite are disclosed.

27 Claims, No Drawings

2-SUBSTITUTED-[2-SUBSTITUTED-AMINO]-N-ARYLALKYL-3-[INDOL-3-YL]

CROSS-REFERENCE TO RELATED APPLICATIONS

This application is a continuation-in-part of copending application Ser. No. 798,068 filed Nov. 14, 1985, now abandoned.

BACKGROUND OF THE INVENTION

The present invention relates to compounds having biological activity as cholecystokinin ligands, to pharmaceutical compositions employing these compounds, and to a method of employing the pharmaceutical compositions in a method of treatment.

More particularly, this invention concerns 2-substituted-[2-substituted-amino]-N-arylalkyl-3-[indol-3-yl]propanamides having demonstrated activity at the central cholecystokinin receptor, with pharmaceutical compositions containing these compounds, and with a method of inhibiting appetite employing the pharmaceutical compositions.

The cholecystokinin (CCK) peptides are widely distributed in various organs of the body including the gastrointestinal tract, endocrine glands, and in the nerves of the peripheral and central nervous systems. Various biologically active forms have been identified including a 33-amino acid hormone and various carboxyl-terminus fragments of this peptide (e.g. the octapeptide $CCK_{26-33}$ and the tetrapeptide $CCK_{30-33}$). (See G. J. Dockray, Br. Med. Bull., 38:, (No. 3): 253-258 (1982)).

The various CCK peptides are thought to be involved in the control of smooth muscle contractility, exocrine and endocrine gland secretion, sensory nerve transmission, and numerous brain functions. Administration of the native peptides causes gall bladder contraction, amylase secretion, excitation of central neurones, inhibition of feeding, anticonvulsive actions and other behavioral effects (See "Cholecystokinin: Isolation, Structure and Functions," G. B. J. Glass, Ed., Raven Press, New York, 1980, pp. 169-221; J. E. Morley, Life Sciences, 27: 355-368 (1980); "Cholecystokinin in the Nervous System," J. de Belleroche and G. J. Dockray, Ed , Ellis Horwood, Chichester, England, 1984, pp. 110-127.

The high concentrations of CCK peptides in many brain areas also indicate major brain functions for these peptides (see G. J. Dockray, Br. Med. Bull., 38 (No. 3): 253-258 (1982)). The most abundant form of brain CCK found is $CCK_{26-33}$, although smaller quantities of $CCK_{30-33}$ exist (see Rehfeld and Gotterman, J. Neurochem., 32: 1339-1341). The role of central nervous system CCK is not known with certainty, but it has been implicated in the control of feeding. (See Della-Fera and Baile, Science, 206: 471-473. )

Currently available appetite suppressant drugs either act peripherally by increasing energy expenditure (such as thyroxine), or in some other manner (such as the biguanides), or act by exerting a central effect on appetite or satiety.

Centrally acting appetite suppressants either potentiate central catecholamine pathways, and tend to be stimulants (for example amphetamine), or influence serotonergic pathways (for example fenfluoramine). Other forms of drug therapy include bulking agents which act by filling the stomach, thereby inducing a "feeling" of satiety

SUMMARY OF THE INVENTION

In accordance with the present invention there are provided compounds having utility as appetite suppressants possessing structural formula 1:

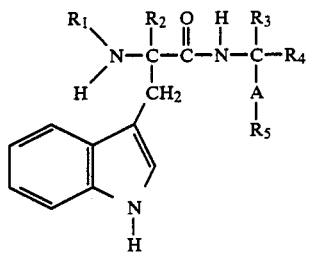

where A is —NH—,

or —$(CH_2)_n$, where n is an integer of from zero to six.

$R_1$ is an N-terminal blocking group selected from

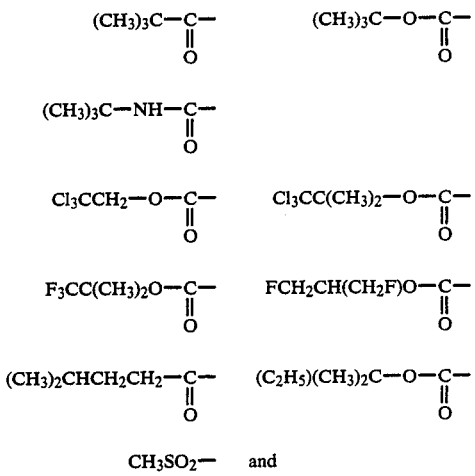

$CH_3SO_2$— and

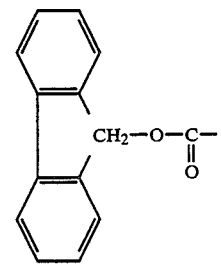

$R_2$ and $R_3$ are independently hydrogen, straight or ranched alkl of from one to six carbon atoms, trifluoromethyl, —$CH_2$—$CH$=$CH_2$, —$CH_2$—C≡CH, —$CH_2OR$, —$(CH_2)_mCOOR$, —$(CH_2)_mNR_6R_7$, —$CH_2Ar$ or —$CH_2OAr$, where m is an integer of from one to six, R, $R_6$, and $R_7$ are elected from hydrogen, or straight or branched alkyl of from one to six carbon atoms, and Ar is 2-, or 3-thienyl, 2-, 3-, or 4-pyridinyl, or

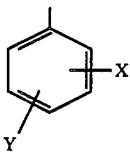

where X and Y are independently hydrogen, fluorine, hlorine, methyl, methoxyl, trifluoromethyl, or nitro, with the provisos that when X is nitro, Y is hydrogen, and $R_2$ and $R_3$ may not both be hydrogen.

$R_4$ is hydrogen, —$CH_2OH$,

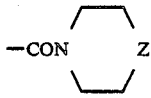

where Z is —$CH_2$—, NR, oxygen, or sulfur, —$CONR_6R_7$, —$CH_2NR_6R_7$, or —COOR where R, $R_6$, and $R_7$ are as previously defined.

$R_5$ is 2- or 3-thienyl, 2-, 3-, or 4-pyridinyl, 2-or 3-indanyl, cyclohexyl, 2- or 3-furanyl, 3- or 4-pyridaninyl, 2-imidazolyl, 2-benzimidazolyl, 2-tetrahydrobenzamidazolyl, 2-eripmidyl, or

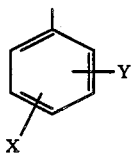

where X and Y are independently hydrogen, fluorine, chlorien, methyl, methoxyl, trifluoromethyl, or nitro, with the proviso that when X is nitro, Y is hydrogen, or a pharmaceutically acceptable salt thereof.

In accordance with another aspect of the present invention, there are provided pharmaceutical compositions containing an amount of a compound as described above effective to suppress the fool intake of a mammal, in combination with a pharmaceutically acceptable carrier.

In yet another aspect, the present invention comprises a method of suppressing the food intake of a mammal comprising administering to a mannal in need of such treatment an apetite suppressing effective maount of a pharmaceutical composition as defined above.

DETAILED DESCRIPTION

The compounds of the present invention are N-terminus-blocked amides, formed by the condensation of two amino acids, but are not "dipeptides" in the classical sense, that term generally being reserved for the product of the coupling of two naturally-occurring α-amino acids. The compounds of the present invention may be called "dipeptoids," that is, dipeptide-like compounds, since they differ from the naturally-occurring natural dipeptides in that the "α-carbon" of the two aminoacids may not both simultaneously carry a hydrogen atom. That is, in structural formula 1 above, the $R_2$ and $R_3$ substituent groups may not both be hydrogen.

Keeping in mind the proviso that $R_2$ and $R_3$ may not both simultaneously be hydrogen, $R_2$ and $R_3$ are selected from hydrogen, straight or branched alkyl of from one to six carbon atoms, —$CH_2CH=CH_2$, —$CH_2C\equiv CH$, —$CH_2Ar$, —$CH_2OR$, —$CH_2OAr$, —$(CH_2)_mCOOR$, or —$(CH_2)_mNR_6R_7$ where m is an integer of from one to six. R is hydrogen or straight or branched alkyl of from one to six carbon atoms, and $R_6$ and $R_7$ are independently hydrogen or straight or branched alkyl of from one to six carbon atoms, and Ar is 2- or 3-thienyl, 2-, 3-, or 4-pyridinyl, or unsubstituted phenyl or mono- or disubstituted phenyl.

In one preferred chemical compound aspect of the present invention, $R_2$ and $R_3$ are independently selected from hydrogen, straight or branched alkyl of from one to six carbon atoms, or trifluoromethyl, with the proviso that $R_2$ and $R_3$ may not both be hydrogen. The most preferred group for $R_2$ is methyl.

$R_1$ may be any one of a number of art-recognized N-terminus blocking groups for amino acids and peptides. These N-terminus blocking groups form a class whose limits are well known to practitioners in the field of amino acid and peptide chemistry. (See, for example, R. Geiger and W. Koenig, "Amine Protecting Groups" in "The Peptides," E. Gross and J. Meienhofer. Eds.. Vol. 3, Academic Press, New York, 1981, pp. 3–136.)

Preferred blocking groups for $R_1$ are the tert-butylcarbonyl group, the tert-butoxycarbonyl (BOC) group, the tert-amyloxycarbonyl (AOC) group, the tert-butylaminocarbonyl group, the 2,2,2-trichloroethoxycarbonyl group, the 2,2,2-trichloro-1,1-dimethylethoxycarbonyl group, the 2,2,2-trifluoromethyl-1,1-dimethylethoxycarbonyl group, the 2-fluoro-1-(fluoromethyl)ethoxycarbonyl group, and the fluoren-9-ylmethyloxycarbonyl group.

$R_4$ may be hydrogen, —$CH_2OR$;

where Z is as previously defined, —$CH_2NR_6R_7$, —COOR, or —$CONR_6R_7$ where R, $R_6$, and $R_7$ are as previously defined. Preferred groups for $R_4$ are hydrogen, hydroxymethyl, and —$CONH_2$.

As defined throughout this specification and the appended claims, the term "straight or branched alkyl" denotes a saturated hydrocarbon group such as methyl, ethyl, n-propyl, iso-propyl, n-, sec-, and tert-butyl, n-pentyl, n-hexyl, and the like.

By virtue of the presence of one or more racemic centers, the compounds of the present invention may exist in various optical isomeric forms. The present invention contemplates all such forms of the compounds. The methods detailed below describe the production of mixtures of diastereomers. Individual diastereomers may be separated from the mixtures thus obtained by conventional techniques such as column chromatography or repetitive recrystallizations. Individual enantiomers may be separated by conventional methods well known to the art such as conversion of the enantiomeric mixture to a mixture of diastereomeric salts by reaction with an optically active salt-forming compound. This is followed by separation of the diastereomeric mixture by chromatographic methods or recrystallization, and reconversion of the salt to the non-salt form by conventional methods.

Specific examples of compounds contemplated as falling within the scope of the present invention include:

N-[(1,1-Dimethylethoxy)carbonyl]-α-DL-methyltryptophyl-L-phenylalaninamide.

N-[(9H-Fluoren-9-ylmethoxy)carbonyl]-α-methyl-DL-tryptophyl-L-phenylalaninamide.

[1-(1H-Indole-3-ylmethyl)-1-methyl-2-oxo-2-[(2-phenylethyl)amino]ethyl]carbamic acid, 1,1-dimethylpropyl ester.

[2-[[1-(Hydroxymethyl)-2-phenylethyl]amino]-1-(1H-indol-3-yl-methyl)-1-methyl)-1-methyl-1oxoethyl]-carbamic acid, 1,1-dimethylpropyl ester.

[2-[[1-(Hydroxymethyl)-2-phenylethyl]amino]-1-[1Hindol-3-ylmethyl)-1-methyl-2-oxoethyl]carbamic acid, 1,1-dimethylpropyl ester.

α-Methyl-N-(4-methyl-1-oxopentyl)-DL-tryptophyl-L-phenylalaninamide.

(±)-[1-(1H-Indol-3-ylmethyl)-1-methyl-2-oxo-2-[(2-phenylethyl)amino]ethyl]carbamic acid, 9H-fluoren-9-ylmethyl ester.

(±)-α-[(2,3-Dimethyl-1-oxobutyl)amino]-α-methyl-N-(2-phenyethy)-1H-indole-3propanamide.

(±)-α-[[[(1,1-Dimethylethyl)amino]carbonyl]amino]-α-methyl-(2-phenylethyl)-1H-indole-3-propanamide.

(±)-[1-(1H-Indol-3-ylmethyl)-2-[[2-(4-methoxyphenyl)ethyl]amino]-1-methyl-2-oxoethyl]carbamic acid, 1,1-dimethylpropyl ester.

(±)-[2-[[2-(4-Chlorophenyl)ethyl]amino]-1-(1H-indol-3-ylmethyl)-1-methyl-2-oxoethyl]carbamic acid, 1,1-dimethylpropyl ester.

(±)-[2-[[2-(3,4-Dichlorophenyl)ethyl]amino]-1-(1H-indol-3-ylmethyl)-1-methyl)-1-methyl-2-oxoethyl]-carbamic acid, 1,1-dimethylpropyl ester.

(±)-[1-(1H-Indol-3-ylmethyl)-1-methyl-2-oxo-[[2-(2-pyridinyl)ethyl]amino]ethyl]carbamic acid, 1,1-dimethylpropyl ester.

(±)-[1-(1H-Indol-3-ylmethyl)-1-methyl-2-oxo-[[2-(2-pyridinyl)ethyl]amino]ethyl]carbamic acid, 2,2,2-trichloro-1,1-dimethylethyl ester.

(R)-[1-(1H-Indol-3-ylmethyl)1-methyl-2-oxo-2-[[2-(2-pyridinyl)ethyl]amino]ethyl]carbamic acid, 2,2,2-trichloro-1,1-dimethylethyl ester.

(±)-[2-[(2,3-Dihydro-1H-inden-1-yl)amino]-1-(1H-indol-3-ylmethyl)-1-methyl-2-oxoethyl]carbamic acid, 2,2,2-trichloro-1,1-dimethylethyl ester.

(±)-[2-[(2,3-Dihydro-1H-inden-2-yl)amino]-1-(1H-indol-3-ylmethyl)-1-methyl-2-oxoethyl]carbamic acid, 2,2,2-trichloro-1,1-dimethylethyl ester (±)-[1-(1H-Indol-3-ylmethyl)-1-[[[2-(2-pyridinyl)-ethyl]amino]carbonyl]propyl]carbamic acid, 2,2,2-trichloroethyl ester.

(S)-[2-[(1,1-Dimethyl-2-phenylethyl)amino]-1-(1H-indol-3-ylmethyl)-2-oxoethyl]carbamic acid, 1,1-dimethylpropylester.

(R)-[2-[(1,1-Dimethyl-2-phenylethyl)amino]-1-(1H-indol-3-ylmethyl)-2-oxoethyl]carbamic acid, 1,1dimethylpropylester.

(±)-[2-[(2-Phenylethyl)amino]-1-(1H-indol-3-yl-methyl)-1-methyl-2-oxoethyl]carbamic acid, 2,2,2-trichloro-1,1-dimethyl ester.

(±)-2-[(2-Phenylethyl)amino]-1-(1H-indol-3-ylmethyl)-1-methyl-2-oxoethyl]carbamic acid, 2,2,2-trichloroethyl ester.

[1-(1HIndol-3-ylmethyl)-1-methyl-2-oxo-2-[[2-oxo-2(1-piperidinyl)-1-(phenylmethyl)ethyl]- amino]ethyl]-carbamic acid, 1,1-dimethylpropyl ester.

[2-[[1-(Hydroxymethyl)-2-phenylethyl]amino]-1-(1H-indol-3ylmethyl)-1-methyl-2-oxoethyl]carbamic acid, 2,2,2-trichloro-1,1-dimethylethyl ester.

[2-[[1-(Hydroxymethyl)-2-phenylethyl]amino]-1-(1H-indol-3-ylmethyl)-1-methyl-2-oxoethyl]carbamic acid, 2,2,2-trichloro-1,1-dimethylethyl ester.

N-[(2,2,2-Trichloro-1,1-dimethylethoxy)carbonyl]-tryptophylphenylalaninamide.

1-(1H-Indol-3-ylmethyl)-1-methyl-2-oxo-2-[[2-(2-pyridinyl)ethyl]amino]ethyl]carbamic acid, 2,2,2-trifluoro-1,1-dimethyl ester.

[1-(1H-Indol-3-ylmethyl)-1-methyl-2-oxo-2-[[2-(2-pyridinyl)ethyl]amino]ethyl]carbamic acid, 2,2-difluoro-1-(fluoromethyl)ethyl ester.

(±)-[2-[(2-Cyclohexylethyl)amino]-1-(1H-indol-3-yl)methyl)-1-methyl-2-oxoethyl]carbamic acid, 1,1-dimethylpropyl ester.

(±)-[1-(1H-Indol-3-ylmethyl)-1-methyl-2-oxo-2-[[2-(3-pyridinyl)ethyl]amino]ethyl]carbamic acid, 1,1-dimethylpropyl ester.

(±)-[1-(1H-Indol-3-ylmethyl)-1-methyl-2-oxo-2-[[2-(4-pyridinyl)ethyl]amino]ethyl]carbamic acid, 1,1-dimethylpropyl ester.

N-[1-(1H-Indol-3-ylmethyl)-1-methyl-2-oxo-2-[(4-phenylbutyl)amino]ethyl]carbamic acid, 1,1-dimethylpropyl ester.

N-[(1,1-Dimethylpropoxy)carbonyl]-DL-tryptophyl-L-phenylalanine, methyl ester.

[2-[[2-Amino-2-oxo-1-(2-thienylmethyl)ethyl]-amino]-1-(1H-indol-3-ylmethyl)-1-methyl-2-oxoethyl]carbamic acid, 1,1-dimethylpropyl ester.

(±)-[2-[[2-(2-Furanyl)ethyl]amino-1-(1H-indol-3-ylmethyl-1-methyl-2-oxoethyl]carbamic acid, 1,1-dimethylpropyl ester.

(±)-[1-(1H-Indol-3-ylmethyl)-1-methyl-2-oxo-2-[[2-(3-pyridazinyl)ethyl]amino]ethyl]carbamic acid, 1,1-dimethylpropyl ester.

(±)-[2-[[2-(1H-Benzimidazol-2-yl)ethyl]ethyl]-amino]-1-(1H-indol-3-ylmethyl)-1-mryhyl-2-oxoryhyl]carbamic acid, 1,1-dimethylpropyl ester.

(±)-[1-(1H-Indol-3-ylmethyl)-1-methyl-2-oxo-2-[(2-thienylethyl)amino]ethyl]carbamic acid, 1,1-dimethylpropyl ester.

[1-(1H-Indol-3-ylmethyl)-1-methyl-2-oxo-2-[[2-(1H-perimidin-2-yl)ethyl]amino]ethyl]carbamic acid, 1,1dimethylpropyl ester.

N-[(2,2,2-Trichloro-1,1-dimethylethoxy)carbonyl]-L-tryptophyl-N$^{\alpha}$-methyl-DL-phenylalaninamide.

The compounds of the present invention are formed by coupling individual substituted amino acids by methods well known in the art. (See, for example, the standard synthetic methods discussed in the multivolume treatise "The Peptides, Analysis, Synthesis, Biology," E. Gross and J. Meienhofer, Eds., Academic Press, New York, 1981.) The individual α-amino acid and N-terminus blocked a-amino acid starting materials are known or commercially available or, if novel, are synthesized by methods within the skill of the art.

For example, compounds of the present invention are prepared by first protecting the N-terminus of an amino acid having the structure 2

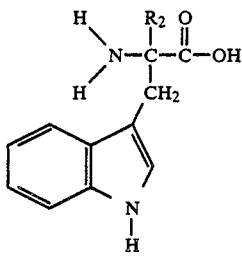

where $R_2$ is as defined above, with the desired blocking group to produce a compound having formula 3

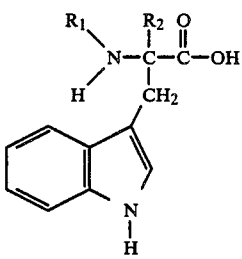

where $R_1$ and $R_2$ are as defined above.

This protected amino acid is then coupled to an amine having the structure

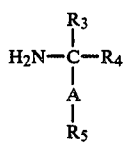

where A, $R_3$, $R_4$, and $R_5$ are as previously defined, in the presence of a coupling reagent such as dicyclohexylcarbodiimide or carbonyl diimidazole to produce the compounds of the present invention. This reaction may also be carried out in the presence of other agents which assist in the coupling reaction, such as pentafluorophenol or hydroxybenzotriazole.

The biological activities of compounds of this invention were evaluated employing an initial screening test which rapidly and accurately measured the binding of the tested compound to known CCK receptor cites. Specific CCK receptors have been shown to exist in the central nervous system. (See Hays et al., *Neuropeptides*, 1: 53–62 (1980); and Sauter et al., *Science*, 208: 1155–1156 (1980).

In the screening test, the cerebral cortices from male CFLP mice weighing between 30–40 g were dissected on ice, weighed and homogenized in 10 volumes of 50 mM Tris-HCl buffer (pH 7.4 at 0°–4° C.). The resulting suspension was centrifuged, the supernate was discarded, and the pellet was washed by resuspension in Tris-HCl buffer followed by recentrifugation.

The final pellet was resuspended in 10 volumes of 10 mM Hepes buffer (pH 7.2 at 23° C.) containing 130 mM NaCl, 4.7 mM KCl, 1 mM EDTA, 5 mg/ml bovine albumin, and bacitracin (0.25 mg/ml).

In saturation studies, cerebral cortical membranes were incubated for 120 minutes in a final volume of 500 μliters of Hepes incubation buffer (pH 7.2) together with 0.1–0.5 nM tritiated-pentagastrin (Amersham Chemical, England).

In the displacement experiments, membranes were incubated with a single concentration (2 nM) of ligand, together with increasing concentrations ($10^{-11}$ to $10^{-6}$ M) of competitive test compound. In each case, the non-specific binding was defined as that persisting in the presence of the unlabeled octapeptide $CCK_{26-33}$ ($10^{-6}$ M).

Following incubation, radioactivity bound to membranes was separated from that free in solution by rapid filtration through Whatman GF/B filters and washed three times with 4-ml portions of ice-cold Tris-HCl buffer. Filters from samples incubated with tritiated pentagastrin were placed in polyethylene vials with 8 ml of scintillation cocktail, and the radioactivity was estimated by scintillation spectrometry (efficiency 47–52%).

The specific binding to CCK receptor sites was defined as the total bound tritiated pentagastrin minus the amount of tritiated pentagrastrin bound in the presence of $10^{-6}$ M octapeptide, $CCK_{26-33}$.

Saturation curves for specific tritiated pentagastrin binding to mouse cortical membranes were analyzed by statisitcal methods to provide estimates for the maximum number of binding sites ($B_{max}$) and the equilibrium dissociation constant ($K_d$).

In the displacement experiements, inhibition curves were analyzed by logit-log plots to provide estimates of the $IC_{50}$ and nH (apparent Hill coefficient) values. $IC_{50}$ values are defined as the concentration of test compound required to produce 50% inhibition of specific binding.

The inhibition constant, $K_i$, of the test compound was then calculated according to the Cheng-Prusoff equation:

$$K_i = \frac{IC_{50}}{1 + [L]/K_d}$$

where [L] is the molar concentration of radiolabel and $K_d$ is the equilibrium dissociation constant.

The $K_i$/M values for several representative compounds of the present invention are presented in Table 1.

The compounds possessing a $K_i$ value of 10 μmolar or less were considered active and were then submitted to a second in vivo screening test in which the ability of the compound to suppress appetite in standard laboratory rats was evaluated.

In this screen, adult male Wistar rats weighing between 250–400 g were housed individually and trained to consume their daily intake of food within a six hour period. Food was then withdrawn for the remaining eighteen hour period of each day. Drinking water was available at all times, and the animals were maintained on a twelve hour light/twelve hour dark cycle. This training regimen was maintained for a seven-day period. Powdered, rather than pelletized, food was used to minimize spillage and to facilitate measurement of food intake.

On each test day, a group of twelve rats was used, six receiving a single dose of test compound and six serving as a control group. Immediately after dosing, the rats were allowed access to food. Food intake was then monitored over the next six-hour period. The food hoppers were weighed at intervals of 30 minutes, and at 1, 2, 3, 4, 5, and 6 hours after administration of the test compound. The percent repression of food intake of laboratory rats under these conditions for the prior art octapeptide, $CCK_{26-33}$, and for several compounds of the present invention appear in Table 2.

In therapeutic use as appetite suppression agents, the compounds utilized in the pharmaceutical method of this invention are administered to the patient at dosage levels of from about 200 to about 2800 mg per day. The specific dosages, however, may be varied depending upon the condition of the patient, the severity of the condition treated, and the activity of the compound being administered. Determination of optimum dosages for a particular patient is within the skill of the art.

For preparing pharmaceutical compositions from the compounds of this invention, inert, pharmaceutically acceptable carriers can be either solid or liquid. Solid form preparations include powders, tablets, dispersable granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogenous mixture is then poured into convenient sized molds and allowed to cool and solidify.

The powders and tablets preferably contain from about 5 to about 70 percent by weight of the active component. Suitable carriers are magnesium carbonate, magnesium stearate, talc, lactose, sugar, pectin, starch, tragacanth, methyl cellulose, sodium carboxymethyl cellulose, a low-melting wax, cocoa butter, and the like.

TABLE 2

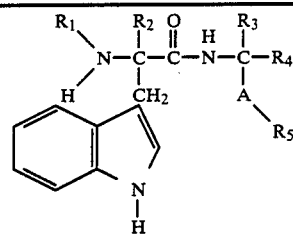

| Compound of Example | Dose | | Percent Repression of Food Intake After | | | |
|---|---|---|---|---|---|---|
| | | | 0.5 | 1.0 | 3.0 | 6.0 |
| | | | Hours | | | |
| $CCK_{26-33}$ (Prior art) | I.P. | 5 mg/kg | 50 | 40 | 3 | 12 |
| 2 | I.P. | 4 mg/kg | 24 | 13 | 19 | 14 |
| 2 | I.P. | 100 mg/kg | 66 | 54 | 1 | 0 |
| 6 | I.P. | 100 mg/kg | 8 | 22 | 36 | 13 |
| 7 | I.P. | 300 mg/kg | 64 | 45 | 23 | 11 |
| 19 | I.P. | 300 mg/kg | 35 | 49 | 60 | 55 |
| 19 | P.O. | 300 mg/kg | 78 | 68 | 52 | 52 |

The term "pharmaceutical preparation" is intended to include the formulation of the active component with encapsulating material as a carrier providing a capsule in which the active component (with or without other carriers) is surrounded by a carrier which is thus in association with it. In a similar manner, cachets are also included.

Tablets, powders, cachets, and capsules can be used as solid dosage forms suitable for oral administration.

Liquid form preparations include solutions, suspensions, and emulsions. Sterile water or water-propylene glycol solutions of the active compounds are examples of liquid preparations suitable for parenteral administration of the compounds of this invention. Liquid preparations can also be formulated in solution in aqueous polyethylene glycol solution.

Aqueous solutions for oral administration of the compounds of this invention can be prepared by dissolving the active compound or a salt thereof in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

TABLE 1

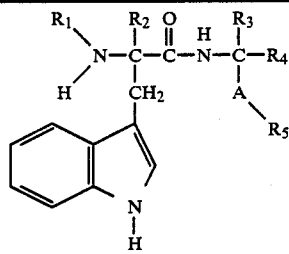

| Example | $R_1$ | $R_2$ | $R_3$ | $R_4$ | $R_5$ | X | $K_i/M$ |
|---|---|---|---|---|---|---|---|
| 2 | BOC* | Methyl | H | —$CONH_2$ | Phenyl | —$(CH_2)$— | $6.0 \times 10^{-6}$ |
| 6 | AOC* | Methyl | H | H | Phenyl | —$(CH_2)$— | $6.5 \times 10^{-6}$ |
| 7 | AOC* | Methyl | H | —$CH_2OH$ | Phenyl | —$(CH_2)$— | $6.8 \times 10^{-6}$ |

*BOC = tert-Butoxycarbonyl
*AOC = tert-Amyloxycarbonyl

Preferably the pharmaceutical preparation is in unit dosage form. In such form, the preparation is divided into unit doses containing appropriate quantities of the active component. The unit dosage form can be a packaged preparation, the package containing discrete quantities of the preparation as, for example, packeted tablets, capsules, and powders in vials or ampoules. The unit dosage form can also be a capsule, cachet, or tablet itself, or it can be the appropriate number of any of these packaged forms.

The following preparative examples are provided as illustrative of the general synthetic methods for preparing compounds of this invention.

EXAMPLE 1

Preparation of N-[(1,1-Dimethylethoxy)carbonyl]-α-methyltryptophyl-L-phenylalaninamide - Mixture of Diastereomers N-tert-Butyloxycarbonyl-α-methyltryptophan (2.29 g, 7.19 mmol) was dissolved in 50 ml of dry, distilled ethyl acetate and 1.38 g (9.0 mmol) of hydroxybenzotriazole, and 0.05 g of 4-dimethylaminopyridine were added. The mixture was cooled to 5° C. and a solution of 1.65 g (8.0 mmol) of dicyclohexylcarbodiimide in 10 ml of ethyl acetate were added. The mixture was stirred for one hour after which 1.77 g (10.8 mmol) of L-phenylalanine and 20 ml of ethyl acetate were added. This mixture was stirred at 5° C. for an additional two hours and then at ambient temperature for thirty-six hours. At the end of this period, 500 μliters of acetic acid were added and after one-half hour the mixture was filtered. The precipitated dicyclohexylurea was washed with ethyl acetate and the filtrates combined.

The yellow-colored organic solution was washed successively with 5% citric acid solution, saturated sodium bicarbonate solution, 5% citric acid solution, and water. The organic layer was separated, dried over anhydrous magnesium sulfate, filtered, and evaporated to yield a light-yellow gummy material which solidified upon standing to an amorphous solid.

Flash chromatography of this crude material on silica gel, eluting with 4% methanol in dichloromethane gave a mixture of diastereomers (2.25 g, 67%).

EXAMPLE 2

Preparation of N-[(1,1-Dimethylethoxy)carbonyl]-α-methyltryptophyl-L-phenylalaninamide-Isomer I Further flash chromatography of the mixture of diastereomers from Example 1 on a silica gel column, eluting with 4% n-propanol in dichloromethane gave a single isomeric product, N-[(1,1-dimethylethoxy)carbonyl] -α-methyltryptophyl-L-phenylalanininamide—Isomer I, as a white solid (0.68 g, 61%).

The 250 MHz proton magnetic resonance spectrum of a deuterochloroform solution of this material exhibited peaks at 1.16 (singlet), 1.37 (singlet), 2.98–3.24 (multiplet), 3.3–3.44 (quartet), 4.7–4.77 (quartet), 4.85 (singlet), 5.35 (singlet), 6.23–6.26 (doublet), and 6.90–8.30 (multiplet) ppm downfield from the tetramethylsilane signal.

Thin-layer chromatography of this material on 0.25 mm-thick Merck Kieselgel 60F-254, eluting with 6% n-propanol in dichloromethane, gave an $R_f$ value of 0.25.

EXAMPLE 3

Preparation of N-[(1,1-Dimethylethoxy)carbonyl]-α-methyltryptophyl-L-phenylalaninamide—Isomer II Further elution of the silica gel column described above in Example 2 produced a second product, N-[(1,1-dimethylethoxy)carbonyl]-α-methyltryptophyl-L-phenylalaninamide—Isomer II, as a white solid.

The 250 MHz proton magnetic resonance spectrum of a deuterochloroform solution of this material exhibited peaks at 1.13 (singlet), 2.9–3.25 (multiplet), 4.2–4.32 (multiplet), 5.7 (singlet), 6.18 (doublet), 6.43 (doublet), and 7.05–7.7 (multiplet) ppm downfield from the tetramethylsilane signal.

Thin-layer chromatography of this material on 0.25 mm-thick Merck Kieselgel 60F-254, eluting with 6% n-propanol in dichloromethane, gave an $R_f$ value of 0.20.

EXAMPLE 4

Preparation of N-[(9H-Fluoren-9-ylmethoxy)carbonyl]-α-methyl-DL-tryptophyl-L-phenylalaninamide Employing the general method of Example 1 above, starting with 0.337 mg of N-[(9H-fluoren-9-ylmethoxy)-carbonyl]-α -methyl-DL-tryptophan, there was obtained 0.397 mg (88%) of a 1:1 mixture of the diastereomeric forms of N-[(9H-fluoren-9-ylmethoxy)carbonyl]-α-methyl-DL-tryptophyl-L-phenylalaninamide, mp 125°–128125°–128° C. (white needles from diethyl ether/hexane.

EXAMPLE 5

Preparation of N-[(9H-Fluoren-9-ylmethoxv)carbonyl-α-methyl-DL-trvtophyl-L-phenylalaninamide - Isomer I Flash chromatography of the mixture of isomers obtained in Example 4 gave one pure isomer of N-[(9H-fluoren-9-ylmethoxy)carbonyl]-α-methyl-DL-tryptophyl-L-phen-Ylalaninamide—Isomer I, as a white solid.

The 250 MHz proton magnetic resonance spectrum of a deuterochloroform solution of this material exhibited peaks at 1.12 (singlet), 3.06–3.08 (doublet), 3.29 (singlet), 4.11 (triplet), 4.32–4.58 (multiplet), 4.71 (quartet), 4.93 (singlet), 5.32 (singlet), 6.15 (doublet), and 6.55–8.0 (multiplet) ppm downfield from the tetramethylsilane signal.

EXAMPLE 6

Preparation of [1-(1H-Indol-3-ylmethyl)-1-methyl-2-oxo-2-[(2-phenylethyl)amino]ethyl]-carbamic acid, 1,1-dimethylpropyl ester Employing the general method of Example 1 above, starting with 0.1 g (0.3 mmol) of tert-amyloxycarbonyl-α-methyltryptophan and 42 μliters (0.33 mmol) of 2-phenylethylamine, there were prepared 0.064 g (49%) of [1-(1H-Indol-3-ylmethyl)-1-methyl-2-oxo-2-[(2-phenylethyl) amino]ethyl]carbamic acid, 1,1-dimethylpropyl ester.

The 250 MHz proton magnetic resonance spectrum of a deuterochloroform solution of this material exhibited peaks at 0.84 (triplet), 1.37 (singlet), 1.51 (singlet), 1.73 (multiplet), 2.64 (triplet), 3.3 (doublet of doublets), 3.44 (multiplet), 5.00 (broad singlet), 6.21 (broad singlet), 6.96–7.60 (multiplet), and 8.28 (broad singlet) ppm downfield from the tetramethylsilane signal.

EXAMPLE 7

Preparation of [2-[[1-(Hydroxymethyl)-2-phenylethyl]-amino]-1-(1H-indol-3-ylmethyl)-1-methyl-2-oxoethyl]-carbamic acid, 1,1-dimethylpropyl ester Employing the general method of Example 1 above, starting with 0.166 g (0.5 mmol) of tert-amyloxycarbonyl-α-methyltryptophan and 0.08 g (0.525 mmol) of β-aminobenzenepropanol, there was obtained, following purification of the crude reaction product by flash chromatography on silica gel, 0.121 g (52%) of [2-[[1-(hydroxymethyl)-2-phenylethyl]-amino]-1-(1Hindol-3-ylmethyl)-1-methyl-2-oxoethyl]carbamic acid, 1,1-dimethylpropyl ester.

The 250 MHz proton magnetic resonance spectrum of a deuterochloroform solution of this material exhibited peaks at 0.86 (multiplet), 1.30 (multiplet), 1.41 (doublet), 1.71 (multiplet), 2.76 (multiplet), 3.27 (multiplet), 3.95 (broad multiplet), 5.05 (doublet), 7.25 (multiplet), and 8.56 (doublet) ppm downfield from the tetramethylsilane signal.

EXAMPLE 8

Preparation of [2-[[1-(Hydroxymethyl)-2-phenylethyl]-amino]-1-(1H-indol-3-ylmethyl)-1-methyl-2-oxoethyl]-carbamic acid, 1,1-dimethylpropyl ester—Isomer I AOC-DL-α-Methyltryptophan (7.5 mmol) was dissolved in dichloromethane and to this solution was added 8 mmol of dicyclohexylcarbodiimide, 16 mmol of hydroxybenzothiazole, and 7.5 mmol of phenylalinol. The resulting mixture was stirred overnight and after this time, the precipitated dicyclohexylurea was removed by filtration.

The filtrate was evaporated to dryness and the residual oil taken up in ethyl acetate. This solution was washed successively with aqueous citric acid solution, saturated sodium bicarbonate solution, and water. The organic layer was separated, dried over anhydrous magnesium sulfate and evaporated to dryness. The crude product was chromatographed on silica gel, eluting with diethyl ether, to yield 9% of [2-[[1-(hydroxymethyl)-2-phenylethyl]-amino]-1-(1H-indol-3-ylmethyl)-1-methyl-2-oxoethyl]carbamic acid, 1,1-dimethylpropyl ester-Isomer I as an amorphous solid.

The proton magnetic resonance spectrum of the material exhibited peaks at 0.8 (triplet), 1.3–1.8 (multiplet), 2.6 (multiplet), 3.3 (multiplet), 4.15 (broad), 5.18 (singlet), 6.23 (doublet), 7.0–7.2 (multiplet), 7.32 (doublet), 7.58 (doublet), and 8.81 (singlet) parts per million downfield from the tetramethylsilane signal.

EXAMPLE 9

Preparation of [2-[[1-(Hydroxymethyl)-2-phenylethyl]-amino]-1-(1H-indol-3-ylmethyl)-1-methyl-2-oxoethyl]-carbamic acid, 1,1-dimethylpropyl ester—Isomer II Continued elution of the column described in Example 8 produced the title compound as an amorphous solid in 8.5% yield.

The proton magnetic resonance spectrum of the material exhibited peaks at 0.8 (triplet), 1.3–1.8 (multiplet), 2.8 (multiplet), 3.3 (multiplet), 4.15 (broad), 5.01 (singlet), 6.23 (doublet), 7.0–7.2 (multiplet), 7.32 (doublet), 7.58 (doublet), and 8.81 (singlet) parts per million downfield from the tetramethylsilane signal.

EXAMPLE 10

Preparation of α-Methyl-N-(4-methyl-1-oxopentyl)-DL-tryptophyl-L-phenylalaninamide The product of Example 5 was treated with a 20% solution of piperidine in dimethylformamide at 5° C. for 30 minutes, after which the solution was evaporated to dryness. The gummy residue was repeatedly triturated with hot petroleum ether, yielding a tan-colored granular solid. This material was dissolved in ethyl acetate and treated with 4-methylpentanoic acid followed by dicyclohexylcarbodiimide. Isolation of the crude product, followed by purification on a silica gel column yielded 47% of α-methyl-N-(4-methyl-1-oxopentyl)-DL-tryptophyl-L-phenylalaninamide, mp 170°–171° C.

EXAMPLE 11

Preparation of (±)-[1-(1H-Indol-3-ylmethyl)-1-methyl-2-oxo-2-[(2-phenylethyl)amino]ethyl]carbamic acid, 9H-fluoren-9-ylmethyl ester Emplying the method of Example 4, but starting with β-phenylethylamine, there was produced (±)-[1-(1H-indol-3-ylmethyl)-1-methyl-2-oxo-2-[(2-phe ethyl]carbamic acid, 9H-fluoren-9-ylmethyl ester, mp 178°–185° C.

EXAMPLE 12 Preparation of (±)-α-Amino-α-methyl-N-(2-phenylethyl)-1H-indole-3-propanamide The product of Example 11 was treated with a 20% solution of piperidine in dimethylformamide at 0° C. for thirty minutes. This solution was evaporated to dryness and the residual oil was triturated with hot petroleum ether to produce a granular solid. This material was dissolved in dilute 2 M hydrochloric acid and extracted with ethyl acetate, the organic layer being discarded. The aqueous layer was made alkaline with 4 M sodium hydroxide solution and extracted with ethyl acetate. The product, (±)-α-amino-α-methyl-N-(2-phenylethyl)-1H-indole-3-propanamide, was isolated as a light tan solid in 83% yield.

The proton magnetic resonance spectrum of the product exhibited peaks at 1.39 (singlet), 2.65 (multiplet), 2.81 (doublet), 3.34 (multiplet), 3.51 (multiplet), 6.94–7.64 (multiplet) and 8.29 (broad singlet) parts per million downfield from the tetramethylsilane signal.

EXAMPLE 13

Preparation of (±)-α-[(2,3-Dimethyl-1-oxobutyl)amino]-α-methyl-N-(2-phenylethyl)-1H-indole-3-propanamide A solution of 0.14 g (1.2 mmol) of tert-butylacetic acid in 5 ml of ethyl acetate was treated with 0.367 g (2.4 mmol) of hydroxybenzothiazole hydrate, and 0.247 g (1.2 mmol) of dicyclohexylcarbodiimide. After stirring at room temperature for one hour, the product of Example 12 (0.321 g, 1 mmol) was added, together with a few additional milliliters of ethyl acetate. This mixture was stirred overnight at room temperature, and the crude product isolated. Following purification by column chromatography on silica gel, there was obtained 0.095 g of (±)-α-[(2,3-dimethyl-1-oxobutyl)-amino ]-α- methyl-N-(2-phenylethyl)-1H-indole-3-propanamide, mp 104°–109° C.

EXAMPLE 14

Preparation of (±)-α-[[[(1,1-Dimethylethyl)amino]-carbonyl ]amino]-α-methyl-N-(2-phenylethyl)-1H-indole-3-propanamide The product of Example 12 (0.25 g, 0.78 mmol) was dissolved in 1.5 ml of dichloromethane and treated with 90 μl (0.78 mmol) of tert-butylisocyanate, and then heated under reflux overnight. The crystalline product, (±)-α-[[[(1,1-dimethylethyl)amino]carbonyl]-amino ]-α-methyl-N-(2-phenylethyl)-1H-indole-3-propanamide, separated and was collected by filtration and dried.

The proton magnetic resonance spectrum of the material exhibited peaks at 1.28 (singlet), 2.68 (multiplet), 3.35 (multiplet), 5.73 (singlet), 5.90 (singlet), 6.95 (multiplet), 7.20 (multiplet), 7.57 (multiplet), and 10.76 (singlet) parts per million downfield from the tetramethylsilane signal.

EXAMPLE 15

Preparation of (±)-[1-(1H-Indol-3-ylmethyl)-2-[[2-(4-methoxyphenyl)ethyl]amino]-1-methyl-2-oxoethyl]-carbamic acid, 1,1-dimethylpropyl ester Employing the method of Example 6, but starting with β-(4-methoxyphenyl)ethylamine and using dichloromethane as the solvent, there was obtained (±)-[1-(1H-indol-3-ylmethyl)-2-[[2-(4-methoxyphenyl)-ethyl ]amino]-1-methyl-2-oxoethyl]carbamic acid, 1,1-dimethylpropyl ester, mp 128°–130° C. in 54% yield.

EXAMPLE 16

Preparation of (±)-[[2-[[2-(4-Chlorophenyl)ethyl]amino]-1-(1H-indol-3-ylmethyl)-1-methyl-2-oxoethyl]carbamic acid, 1,1-dimethylpropyl ester Employing the method of Example 6, but starting with β-(4-chlorophenyl)ethylamine and using dichloromethane as the solvent, there was obtained (±)-[2-[[2-(4-chlorophenyl)ethyl]amino]-1-(1H-indol-3-ylmethyl)-1-methyl-2-oxoethyl]carbamic acid, 1,1-dimethylpropyl ester, mp 150°–153° C. in 48% yield.

EXAMPLE 17

Preparation of (±)-[2-[[2-(3,4-Dichlorophenyl)ethyl]-amino ]-1-(1H-indol-3-ylmethyl)-1-methyl-2-oxoethyl]-carbamic acid, 1,1-dimethylpropyl ester Employing the method of Example 6, but starting with 2-(3,4-dichlorophenyl)ethylamine and using dichloromethane as the solvent, there was obtained (±)-2-[[2-(3,4-dichlorophenyl)ethyl]amino]-1-(1H-indol-3-ylmethyl)-1-methyl-2-oxoethyl]carbamic acid, 1,1-dimethylpropyl ester, mp 139°–142° C. in 74% yield.

EXAMPLE 18

Preparation of (±)-[1-(1H-Indol-3-ylmethyl)-1-methyl-2-oxo-2-[[2-(2-pyridinyl)ethyl]amino]ethyl]carbamic acid, 1,1-dimethylpropyl ester Employing the method of Example 6, but starting with 2-(2-pyridinyl)ethylamine, there was obtained (±)-[1-(1H-indol-3-ylmethyl)-1-methyl-2-oxo-2-[[2-(2-pyridinyl)ethyl]amino]ethyl]carbamic acid, 1,1-dimethylpropyl ester, mp 151°–152° C. in 27% yield.

EXAMPLE 19

Preparation of (±)-[1-(1H-Indol-3-ylmethyl)-1-methyl-2-oxo-2-[[2-(2-pyridinyl)ethyl]amino]ethyl]carbamic acid, 2,2,2-trichloro-1,1-dimethylethyl ester Employing the method of Example 6, but starting with trichlorobutoxycarbonyl-DL-α-methyltryptophan and 2-(2-pyridinyl)ethylamine, there was obtained (±)-[1-(1H-indol-3-ylmethyl)-1-methyl-2-oxo-2-[[2-(2-pyridinyl)ethyl]amino]ethyl]carbamic acid, 2,2,2-trichloro-1,1-dimethylethyl ester, mp 130°–133° C. as a white powder in 60% yield.

EXAMPLE 20

Preparation of (R)-[1-(1H-Indol-3-ylmethyl)-1-methyl-2-oxo-2-[[2-(2-pyridinyl)ethyl]amino]ethyl]carbamic acid, 2,2,2-trichloro-1,1-dimethylethyl ester Employing the method of Example 19, but starting with trichlorobutoxycarbonyl-D-α-methyltryptophan, there was obtained (R)-[1-(1HH-indol-3-ylmethyl)-1-methyl-2-oxo-2-[[2-(2-pyridinyl)ethyl]amino]ethyl]carbamic acid, 2,2,2-trichloro-1,1-dimethylethyl ester, mp 154°–157° C. in 77% yield.

EXAMPLE 21

Preparation of (±)-[2-[(2,3-Dihydro-1H-inden-1-yl)amino-]-1-(1H-indol-3-ylmethyl)-1-methyl-2-α-xoethyl]-carbamic acid, 2,2,2-trichloro-1,1-dimethylethyl ester A solution of trichlorobutoxycarbonyl-DL-o-methyltryptophan (0.422 g, 1.0 mmol) in 10 ml of dichloromethane was treated with 0.203 mg (1.1 mmol) of pentafluorophenol followed by 0.216 mg (1.05 mmol) of dicyclohexylcarbodiimide. The resulting mixture was stirred at room temperature for thirty minutes. After this time, a solution of 0.15 g (1.13 mmol) of 1-aminoindane in 5 ml of dichloromethane was added, and stirring was continued for five hours.

At the end of this time, the solution was evaporated and the residue triturated with ethy acetate, and then filtered to remove the dicyclohexylurea. Evaporation left a gum which was purified by column chromatography to produce (±)-[2-[(2,3-dihydro-1H-inden-1-yl)amino]-1-(1H-indol-3-ylmethyl)-1-methyl-2-oxoethyl]carbamic acid, 2,2,2-trichloro-1,1-dimethylethyl ester in 73% yield as a hard, colorless foamy material.

The proton magnetic resonance spectrum of the material exhibited peaks at 1.61 (multiplet), 1.90 (multiplet), 2.50 (multiplet), 2.84 (multiplet), 3.48 (multiplet), 5.46 (multiplet), 6.19 (broad triplet), 6.97–7.25 (multiplet), 7.34 (doublet), 7.61 (doublet), and 8.17 (broad singlet) parts per million downfield from the tetramethylsilane signal.

EXAMPLE 22

Preparation of
(±)-[2-(2,3-Dihydro-1H-inden-2-yl)amino-]-1-(1H-indol-3-ylmethyl)-1-methyl-2-oxoethyl]carbamic acid, 2,2,2-trichloro-1,1-dimethylethyl ester Employing the method of Example 21, but starting with 2-aminoindane and adding 1.1 milliequivalents of triethylamine, there was obtained (±)-[2-[(2,3-dihydro-1H-inden-2-yl)amino]-1-(1H-indol-3-ylmethyl)-1-methyl- 2-oxoethyl]carbamic acid, 2,2,2-trichloro-1,1-dimethylethyl ester in 71% yield as a hard white foam.

The proton magnetic resonance spectrum of the material exhibited peaks at 1.55 (singlet), 1.84 (doublet), 2.51 (multiplet), 3.31 (multiplet), 4.56 (multiplet), 5.44 (singlet), 6.17 (broad doublet), 6.95–7.61 (multiplet), and 8.13 (broad singlet) parts per million downfield from the tetramethylsilane signal.

EXAMPLE 23

Preparation of
(±)-1-(1H-Indol-3-ylmethyl)-1-[[[2-(2-pyridinyl)ethyl]amino]carbonyl]propyl]carbamic acid, 2,2,2-trichloroethyl ester A solution of 0.10 g (0.43 mmol) of DL-α-methyltryptophan in 5 ml of water was treated with 0.095 g (0.9 mmol) of sodium carbonate, and stirred while slowly adding a solution of 0.106 g (0.5 mmol) of trichloroethoxycarbonyl chloride in 3 ml of dioxane. The resulting mixture was stirred for three hours, after which the dioxane was removed under vacuum and the residue diluted with 5 ml of water. The aqueous solution was extracted with 5 ml of ethyl acetate, and the organic solution discarded. The aqueous layer was acidified with dilute aqueous citric acid and extracted with ethyl acetate. The organic layer was separated, dried and evaporated to yield an oil.

This oil was dissolved in 5 ml of dichloromethane and treated with 0.092 g (0.5 mmol) of pentafluorophenol and 0.103 g (0.5 mmol) of dicyclohexylcarbodiimide and stirred for thirty minutes.

2-(2-Pyridinyl)ethylamine (0.061 g, 0.5 mmol) was added and the resulting mixture was stirred overnight. The crude product was then isolated and purified by column chromatography to yield (±)-[1-(1H-indol-3-ylmethyl)-1-[[[2-(2-pyridinyl)ethyl]amino]carbonyl]propyl]carbamic acid, 2,2,2-trichloroethyl ester as a light tan solid, mp 151°–154° C. in 16% yield.

EXAMPLE 24

Preparation of
(S)-[2-[(1,1-DimethYl-2-phenylethyl)amino-]-1-(1H-indol-3-ylmethyl)-2-oxoethyl]carbamic acid, 1,1-dimethylpropyl ester A solution of tert-amyloxycarbonyl-L-tryptophan (0.32 g, 1.0 mmol) in 10 ml of dichloromethane was treated at room temperature with 0.185 g (1.0 mmol) of pentafluorophenol and 0.22 g (1.1 mmol) of dicyclohexylcarbodiimide over a period of thirty minutes.

To this mixture was added a solution of 0.205 g (1.1 mmol of phentermine hydrochloride in 5 ml of dichloromethane to which 0.110 g (1.1 mmol of triethylamine had been previously added.

After stirring this mixture for thirty-six hours, the crude product was isolated and purified by column chromatography to yield 54% of (S)-[2-[(1,1-dimethyl-2-phenylethyl)amino]-1-(1H-indol-3-ylmethyl)-2-oxoethyl]carbamic acid, 1,1-dimethylpropyl ester as a hard white foam.

The proton magnetic resonance spectrum of the material exhibited peaks at 0.88 (triplet), 1.12 (doublet), 1.39 (singlet), 1.78 (multiplet), 2.82 (doublet of doublets), 3.18 (broad multiplet), 4.30 (broad multiplet), 5.31 (broad singlet), 6.87–7.36 (multiplet), 7.67 (doublet), and 8.40 (broad singlet) parts per million downfield from the tetramethylsilane signal.

EXAMPLE 25

Preparation of
(R)-[2-[(1,1-Dimethyl-2-phenylethyl)amino]-1-(1H-indol-3-ylmethyl)-2-oxoethyl]carbamic acid, 1,1-dimethylpropyl ester Using the method of Example 24, but starting with tert-amyloxycarbonyl-D-tryptophan, there was obtained (R)-[2-[(1,1-dimethyl-2-phenylethyl)amino]-1-(1H-indol-3-ylmethyl)-2-oxoethyl]carbamic acid, 1,1-dimethylpropyl ester in 57% yield.

The proton magnetic resonance spectrum of the material exhibited peaks at 0.84 (triplet), 1.12 (doublet), 1.39 (singlet), 1.48 (singlet), 1.61 (multiplet), 2.81 (doublet of doublets), 3.19 (broad multiplet), 4.30 (broad multiplet), 5.31 (broad singlet), 6.84–7.38 (multiplet), 7.68 (doublet), and 8.24 (broad singlet) parts per million downfield from the tetramethylsilane signal.

EXAMPLE 26

Preparation of
(±)-[2-[(2-Phenylethyl)amino]-1-(1H-indol-3-ylmethyl)-1-methyl-2-oxoethyl]carbamic acid, 2,2,2-trichloro-1,1-dimethyl ester The product from Example 11 was acylated under Schotten-Baumann conditions using trichloro-tert-butoxycarbonyl chloride in a rapidly stirred dioxane/4M sodium hydroxide mixture.

The product, (±)-[2-[(2-phenylethyl)amino]-1-(1H-indol-3-ylmethyl)-1-methyl-2-oxoethyl]carbamic acid, 2,2,2-trichloro-1,1-dimethyl ester, mp 132°–134° C., was isolated as a white granular solid in 82% yield.

EXAMPLE 27

Preparation of
(±)-[2-[(2-Phenylethyl)amino]-1-(1H-indol-3-ylmethyl)-1-methyl-2-oxoethyl]carbamic acid, 2,2,2-trichloroethyl ester The product from Example 11 was acylated under Schotten-Baumann conditions using trichloroethoxycarbonyl chloride in a rapidly stirred dioxane/4M sodium hydroxide mixture.

The product, (±)-[2-[(2-phenylethyl)amino]-1-(1H-indol-3-ylmethyl)-1-methyl-2-oxoethyl]carbamic acid, 2,2,2-trichloroethyl ester, was isolated as a hard white foamy solid in 80% yield.

The proton magnetic resonance spectrum of the material exhibited peaks at 1.61 (singlet), 2.61 (triplet), 3.39 (multiplet), 4.67 (doublet of doublets), 5.85 (broad multiplet), 6.96–7.57 (multiplet), and 8.13 (broad singlet) parts per million downfield from the tetramethylsilane signal.

EXAMPLE 28

Preparation of
[1-(1H-Indol-3-ylmethyl)-1-methyl-2-oxo-2-[[2-oxo-2-(1-piperidinyl)-1-(phenylmethyl)ethyl]-amino ethyl]carbamic acid, 1,1-dimethylpropyl ester Using the method of Example 6, but starting with L-phenylamine piperidide, there was obtained [1-(1H-indol-3-ylmethyl)-1-methyl-2-oxo-2-[[2-oxo-2-(1-piperidinyl)-1-(phenylmethyl)ethyl]amino]ethyl]carbamic acid, 1,1-dimethylpropyl ester as a hard white foam in 54% yield.

The proton magnetic resonance spectrum of the material exhibited peaks at 0.86 (multiplet), 1.35–1.47 (multiplet), 1.76 (multiplet), 2.82–3.59 (multiplet), 5.10 (multiplet), 6.99–7.35 (multiplet), 7.59 (multiplet), and 8.18(broad singlet) parts per million downfield from the tetramethylsilane signal.

EXAMPLE 29

Preparation of
2-[[1-(Hydroxymethyl)-2-phenylethyl]-amino]-1-(1H-indol-3-ylmethyl)-1-methyl-2-oxoethyl]carbamic acid, 2,2,2-trichloro-1,1-dimethylethyl ester Employing the method of Example 19, a mixture of the [R-(R*,S*)]and [S-(R*,R*)]isomers was prepared. Purification of the mixture by column chromatography yielded "Isomer I" as a hard white foam in 28% yield.

The proton magnetic resonance spectrum of the material exhibited peaks at 1.54 (singlet), 1.85 (doublet), 2.42 (broad singlet), 2.68 (doublet), 3.16 (doublet of doublets), 3.52 (broad multiplet), 4.08 (broad multiplet), 5.51 (singlet), 6.00 (doublet), 6.93 (doublet), 6.93–7.59 (multiplet), and 8.15 (broad singlet) parts per million downfield from the tetramethylsilane signal.

EXAMPLE 30

Preparation of
[2-[[1-(Hydroxymethyl)-2-phenylethyl]amino]-1-(1H-indol-3-ylmethyl)-1-methyl-2-oxoethyl]carbamic acid, 2,2,2-trichloro-1,1-dimethylethyl ester pentanedioate salt The material obtained from Example 29 (0.36 g, 0.68 mmol) was dissolved in 5 ml of dry ethyl acetate and treated with 0.078 g (0.68 mmol) of glutaric anhydride and the mixture heated under reflux overnight.

Evaporation of the mixture, followed by purification of the crude reaction product by column chromatography yielded [2-[[1-(hydroxymethyl)-2-phenylethyl]amino]-1-(1H-indol-3-ylmethyl)-1-methyl-2-oxoethyl]-carbamic acid, 2,2,2-trichloro-1,1-dimethylethyl ester pentanedioate salt (2:1) as a hard white foam in 43% yield.

The proton magnetic resonance spectrum of the material exhibited peaks at 1.52 (doublet), 1.86 (multiplet), 2.31 (broad multiplet), 2.66 (multiplet), 3.30 (multiplet), 3.77 (broad singlet), 4.34 (broad singlet), 5.68 (broad singlet), 6.40 (broad doublet), 6.95–7.57 (multiplet), and 8.60 (broad singlet) parts per million downfield from the tetramethylsilane signal.

EXAMPLE 31

Preparation of
N-[(2,2,2-Trichloro-1,1-dimethylethoxy)carbonyl]tryptophylphenylalaninamide—Isomer I Following the method of Example 19, and purification of the crude reaction product by column chromatography on silica gel, there was obtained one isomer of N-[(2,2,2-trichloro-1,1-dimethylethoxy)carbonyl]tryptophylphenylalaninamide, ("isomer I"), mp 187° C. in 47% yield.

EXAMPLE 32

Preparation of
[1-(1H-Indol-3-ylmethyl)-1-methyl-2-oxo-2-[[2-(2-pyridinyl)ethyl]amino]ethyl]carbamic acid, 2,2,2-trifluoro-1,1-dimethyl ester Step 1—Preparation of 1H-imidazole-1-carboxylic acid, 2,2,2-trifluoro-1,1-dimethylethyl ester 1,1-Carbonyldiimidazole (6.3 g, 39 mmol) was dissolved in 100 ml of dry toluene heated to reflux. A solution of 1,1,1-trifluoro-2-methyl-2-propanol (2 g, 15.5 mmol) in 80 ml of toluene was added dropwise. The mixture was stirred for two hours.

After this time, the toluene was evaporated to yield 9.6 g of 1H-imidazole-1-carboxylic acid, 2,2,2-trifluoro-1,1-dimethylethyl ester as a white solid.

Step 2—Preparation of N-(2,2,2-Trifluoro-1,1-dimethylethoxycarbonyl)-α-methyltryptophan methyl ester One-half gram of the crude reaction product of Step 1 above (containing approximately 0.17 g, 0.77 mmol of the desired material) was dissolved in 3 ml of dioxane, and the solution was heated to reflux. A solution of α-methyltryptophan methyl ester (0.35 g, 1.45 mmol) in 5 ml of dioxane was added dropwise over a one-half hour period. The mixture was heated and stirred under reflux for two days, after which time there were added an additional 0.175 g (0.77 mmol) of α-methyltryptophan methyl ester. Stirring and heating of this mixture was continued for an additional twenty-four hours.

The mixture was then evaporated and 30 ml of ethyl acetate were added, and the brown-colored solution was washed successively with portions of saturated sodium bicarbonate solution, and brine. The organic layer was separated, dried over anhydrous magnesium sulfate, and evaporated to yield a brown oil.

The crude reaction product was chromatographed on a silica gel column, eluting with 25% ethyl acetate in hexane to produce 100 mg of N-(2,2,2-trifluoro-1,1-dimethylethoxycarbonyl)-α-methyltryptophan methyl ester as a straw-colored oil.

The proton magnetic resonance spectrum of the material exhibited peaks at 1.25 (singlet), 1.7 (doublet), 3.0–3.5 (multiplet), 3.70 (singlet), and 6.9–7.7 (multiplet) parts per million downfield from the tetramethylsilane signal.

Step 3—Preparation of
N-(2,2,2-Trifluoro-1,1-dimethylethoxycarbonyl)-α-methyltryptophan N-(2,2,2-trifluoro-1,1-dimethylethoxycarbonyl)-α-methyltryptophan methyl ester (0.1 g, 0.29 mmol) was dissolved in 3 ml of dioxane. To this solution was added 0.04 g (0.95 mmol) of lithium hydroxide dissolved in 2 ml of water. This mixture was stirred at ambient temperature for twenty-four hours.

At the end of this period, the mixture was evaporated and 5 ml of water were added. The solution was acidified by the addition of 2 M hydrochloric acid, and the acidified mixture was extracted five times with ethyl acetate.

The combined organic extracts were washed with brine, dried over anhydrous magnesium sulfate, and evaporated to yield 70 mg (73%) of N-(2,2,2-trifluoro-1,1-dimethylethoxycarbonyl)-α-methyltryptophan as a green oil.

The proton magnetic resonance spectrum of the material exhibited peaks at 1.6–1.7 (triplet), 3.3–3.5 (multiplet), 7.0–7.8 (multiplet), and 9.25 (broad) parts per million downfield from the tetramethylsilane signal.

Step 4—Preparation of
[1-(1H-Indol-3-ylmethyl)-1-methyl-2-oxo-2-[[2-(2-pyridinyl)ethyl]amino]ethyl]carbamic acid, 2,2,2-trifluoro-1,1-dimethyl ester A solution of N-(2,2,2-trifluoro-1,1-dimethylethoxycarbonyl)-α-methyltryptophan (0.06 g, 0.16 mmol) in 2 ml of ethyl acetate was cooled in an ice bath and then treated successively with 30 μl (0.17 mmol) of triethylamine and 28 μl (0.17 mmol) of isobutyl chloroformate. After forty-five minutes, the mixture was further treated with a solution of 25.7 μl (0.17 mmol) of 2-(2-pyridinyl)ethylamine in 2 ml of ethyl acetate. After one hour, the reaction mixture was allowed to warm to room temperature and was stirred at this temperature for eighteen hours.

At the end of this time, precipitated solids were removed by filtration and the solution was washed successivly with portions of saturated sodium bicarbonate and brine, dried, and evaporated to yield 40 mg of a green oil. This crude product was purified by column chromatography on silica gel, eluting with 25% ethyl acetate in hexane to produce 15 mg of a yellow oil which was crystallized from dichloromethane/hexane to yield [1-(1H-indol-3-ylmethyl)-1-methyl-2-oxo-2-[[2-(2-pyridinyl)ethyl]amino]ethyl]carbamic acid, 2,2,2-trifluoro-1,1-dimethyl ester as an amorphous yellow solid.

The proton magnetic resonance spectrum of this material exhibited peaks at 1.6 (singlet), 1.62 (singlet), 2.8 (triplet), 3.35 (singlet), 3.60 (triplet), 6.9–7.6 (multiplet), 8.15 (singlet), and 8.4 (doublet) parts per million downfield from the tetramethylsilane signal.

EXAMPLE 33

Preparation of
[1-(1H-Indol-3-ylmethyl)-1-methyl-2-oxo-2-[[2-(2-pyridinyl)ethyl]amino]ethyl]carbamic acid, 2,2-difluoro-1-(fluoromethyl)ethyl ester Employing the four-step method detailed in Example 32, but employing 70 mg of N-(1,3-difluoroisopropoxycarbonyl)-α-methyltryptophan at Step 4, there were obtained 11 mg of [1-(1H-indol-3-ylmethyl)-1-methyl-2-oxo-2-[[2-(2-pyridinyl)ethyl]amino]ethyl]carbamic acid, 2,2-difluoro-1-(fluoromethyl)ethyl ester as a pale yellow solid, mp 65°–67° C., recrystallized from dichloromethane/hexane.

EXAMPLE 34

Preparation of
(±)-[2-[(2-Cyclohexylethyl)amino]-1-(1H-indol-3-yl)methyl)-1-methyl-2-oxoethyl]carbamic acid, 1,1-dimethylpropyl ester tert-Amyloxycarbonyl-α-methyltryptophan (1 mmol) was dissolved in 3 ml of ethyl acetate, and 1.9 mmol of hydroxybenzotriazole was added. This mixture was stirred for three hours at room temperature. To this mixture was then added 1 mmol of 2-(cyclohexyl)ethylamine (1 mmol) and the mixture stirred at room temperature for two days.

The dicyclohexylurea which separated was removed by filtration, and the filtrate was washed successively with portions of aqueous citric acid solution and sodium bicarbonate. The organic solution was dried over anhydrous magnesium sulfate and evaporated. The residual oil was chromatographed on a silica gel column, eluting with 50:1 dichloromethane/methanol to yield (±)-[2-[(2-yclohexylethyl)amino]-1-(1H-indol-3-yl) methyl)-1-methyl-2-oxoethyl]carbamic acid, 1,1dimethylpropyl ester, mp 129.5°–131° C. in 35% yield.

EXAMPLE 35

Preparation of
(±)-[1-(1H-Indol-3-ylmethyl)-1-methyl-2-oxo-2[[2-(3-pyridinyl)ethyl]amino]ethyl]carbamic acid, 1,1dimethylpropyl ester Employing the method of Example 8, but starting with 2-(3-pyridinyl)ethylamine, there was obtained [1-(1H-indol-3-ylmethyl)-1-methyl-2-oxo-2-[[2-(3-pyridinyl)ethyl]amino]ethyl]carbamic acid, 1,1-dimethylpropyl ester, mp 95°–105° C. in 24% yield.

EXAMPLE 36

Preparation of
(±)-[1-(1H-Indol-3-ylmethyl)-1-methyl-2-oxo-2-[[2-(4-pyridinyl)ethyl]amino]ethyl]carbamic acid, 1,1-dimethylpropyl ester Employing the method of Example 8, but starting with 2-(4-pyridinyl)ethylamine, there was obtained [1-(1H-indol-3-ylmethyl)-1-methyl-2-oxo-2-[[2-(4-pyridinyl)ethyl]amino]ethyl]carbamic acid, 1,1-dimethylpropyl ester, mp 138°–141° C. in 18% yield.

EXAMPLE 37

Preparation of
N-[1-(1H-Indol-3-ylmethyl)-1-methyl-2-oxo-2-[(4-phenylbutyl)amino]ethyl]carbamic acid, 1,1-dimethylpropyl ester Employing the method of Example 8, but starting with 4-(phenyl)butylamine, there was obtained N-[1-(1H-indol-3-ylmethyl)-1-methyl-2-oxo-2-[(4-phenylbutyl)amino]ethyl]carbamic acid, 1,1-dimethylpropyl ester, mp 127°–130° C., recrystallized from ethyl acetate/hexane.

EXAMPLE 38

Preparation of
N-[(1,1-Dimethylpropoxy)carbonyl]-DL-tryptophyl-L-phenylalanine, methyl ester Employing the method of Example 8, but starting with L-phenylalanine, methyl ester, there was obtained N-[(1,1-dimethylpropoxy)carbonyl]-DL-tryptophyl-L-phenylalanine, methyl ester, mp 55°–57° C. in 22% overall yield.

EXAMPLE 39

Preparation of
[2-[[2-Amino-2-oxo-1-(2-thienylmethyl)ethyl]amino]-1-(1H-indol-3-ylmethyl)-1-methyl-2-oxoethyl]carbamic acid, 1,1-dimethylpropyl ester Employing the method of Example 8, but starting with 2-thienylalaninamide, there was obtained [2-[[2-amino-2-oxo-1-(2-thienylmethyl)ethyl]amino]-1-(1H-indol-3-ylmethyl)-1-methyl-2-oxoethyl]carbamic acid, 1,1-dimethylpropyl ester, mp 187°-192° C. in 44% yield.

EXAMPLE 40

Preparation of (±)-[2-[[2-(2-Furanyl)ethyl]amino-1-(1H-indol-3-ylmethyl)-1-methyl-2-oxoethyl]carbamic acid, 1,1-dimethylpropyl ester Employing the method of Example 8, but starting with 2-(2-furanyl)ethylamine, there was obtained (±)-[2-[[2-(2-furanyl)ethyl]amino-1-(1H-indol-3-ylmethyl)1-methyl-2-oxoethyl]carbamic acid, 1,1-dimethylpropyl ester, mp 84°-86° C. in 47% overall yield.

EXAMPLE 41

Preparation of (±)-1-(1H-Indol-3-ylmethyl)-1-methyl-2-oxo-2-[[2-(3-pyridazinyl)ethyl]amino]ethyl]carbamic acid, 1,1-dimethylpropyl ester Employing the method of Example 8, but starting with 2-(2-pyridazinyl)ethylamine, there was obtained (±)-[1-(1H-Indol-3-ylmethyl)-1-methyl-2-oxo-2-[[2- (3-pyridazinyl)ethyl]amino]ethyl]carbamic acid, 1,1-dimethylpropyl ester, mp 85°-88° C. in 45% yield.

EXAMPLE 42

Preparation of (±)-[2-[[2-(1H-Benzimidazol-2-yl)ethyl]ethyl]amino]-1-(1H-indol-3-ylmethyl)-1-methyl-2-oxoethyl]carbamic acid, 1,1-dimethylpropyl ester Employing the method of Example 8, but starting with 2-(2-benzimidazolyl)ethylamine, there was obtained (±)-[2-[[2-(1H-benzimidazol-2-yl)ethyl]ethyl]amino]-1-(1H-indol-3-ylmethyl)-1-methyl-2-oxoethyl]carbamic acid, 1,1-dimethylpropyl ester, mp 100°-110° C. in 63% yield.

EXAMPLE 43

Preparation of (±)-1-(1H-Indol-3-ylmethyl)-1-methyl-2-oxo-2-[(2-thienylethyl)amino]ethyl]carbamic acid, 1,1-dimethylpropyl ester Employing the method of Example 8, but starting with 2-(2-thienyl)ethylamine, there was obtained (±)-[1-(1H-Indol-3-ylmethyl)-1-methyl-2-oxo-2-[(2-thienylethyl)amino]ethyl]carbamic acid, 1,1-dimethylpropyl ester mp 95°-98° C. in 61% yield.

EXAMPLE 44

Preparation of [1-(1H-Indol-3-ylmethyl)-1-methyl-2-oxo-2-[[2-(1H-perimidin-2-yl)ethyl]amino]ethyl]-carbamic acid, 1,1-dimethylpropyl ester Employing the method of Example 8, but starting with 2-(2-perimidinyl)ethylamine, there was obtained [1-(1H-indol-3-ylmethyl)-1-methyl-2-oxo-2-[[2-(1H-perimidin-2-yl)ethyl]amino]ethyl]carbamic acid, 1,1-dimethylpropyl ester, mp >160° C. (dec.)

EXAMPLE 45

Preparation of N-[(2,2,2-Trichloro-1,1-dimethylethoxy)carbonyl]-L tryptophyl--N$^\alpha$-methyl-DL-phenylalaninamide Employing the method of Example 8, but starting with DL-α-methylphenylalanine and tert-butyloxycarbonyl-L-tryptophan, reacted under reflux for a period of 7 days, there was obtained N-[(2,2,2-trichloro-1,1-dimethylethoxy)carbonyl]-L-tryptophyl-N$^\alpha$-methyl-DL-phenylalaninamide, mp 100°-105° C.

I claim:

1. A compound having structural formula 1:

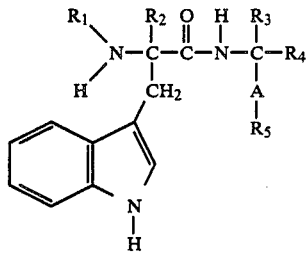

wherein A is —NH—,

or —(CH$_2$)$_n$, where n is an integer of from zero to six;

R$_1$ is an N-terminal blocking group selected from

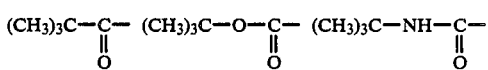

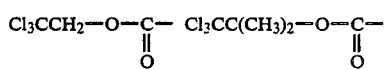

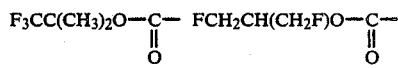

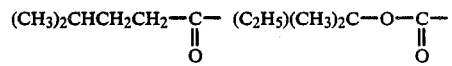

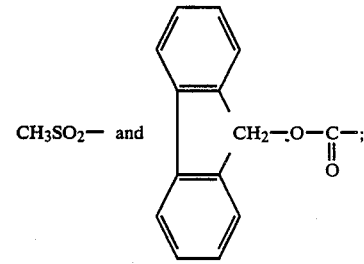

R$_2$ is straight or branched alkyl of from one to six carbon atoms, trifluoromethyl, —CH$_2$—CH=CH$_2$, —CH$_2$—C≡CH, —CH$_2$OR, —(CH$_2$)$_m$COOR, —(CH$_2$)$_m$NR$_6$R$_7$, —CH$_2$Ar or -CH$_2$OAr, where m is an integer of from one to six, R, R$_6$, and R$_7$ are selected from hydrogen, or straight or branched alkyl of from one to six carbon atoms, and Ar is 2-, or 3-thienyl, 2-, 3-, or 4-pyridinyl, or

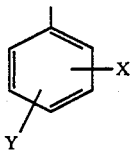

where X and Y are independently hydrogen, fluorine, chlorine, methyl, methoxyl, trifluoromethyl, or nitro, with the provisos that when X is nitro, Y is hydrogen, and R₃ is hydrogen, straight or branched alkyl of from one to six carbon atoms, trifluoromethyl, —CH₂—CH=₂, CH=—CH₂—C≡CH, —CH₂OR, —(CH₂)ₘCOOR, —(CH₂)ₘNR₆R₇, —CH₂Ar or —CH₂OAr, where m is an integer of from one to six, R, R₆, and R₇ are selected from hydrogen, or straight or branched alkyl of from one to six carbon atoms, and Ar is 2-, or 3-thienyl, 2-, 3-, or 4-pyridinyl, or

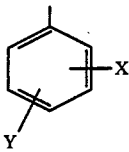

where X and Y are independently hydrogen, fluorine, chlorine, methyl, methoxyl, trifluoromethyl, or nitro, with the provisos that when X is nitro, Y is hydrogen, and R₄ is hydrogen, —CH₂OH,

where Z is —CH₂—, NR, where R is as previously defined, oxygen, sulfur —CONR₆R₇, —CH₂NR₆R₇, or —COOR where R, R₆, and R₇ are as previously defined, and R₅ is 2- or 3-thienyl, 2-, 3-, or 4-pyridinyl, 2- or 3-indanyl, cyclohexyl, 2- or 3-furanyl, 3- or 4-pyridazinyl, 2-imidazolyl, 2-benzimidazolyl, 2-tetrahydrobenzimidazolyl, 2-perimidyl, or

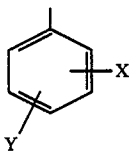

where X and Y are independently hydrogen, fluorine, chlorine, methyl, methoxyl, trifluoromethyl, or nitro, with the proviso that when X is nitro, Y is hydrogen, or a pharmaceutically acceptable salt thereof.

2. A compound as defined by claim 1 wherein R₂ is methyl.

3. A compound as defined by claim 1 wherein R₄ is hydrogen, hydroxymethyl, or —CONH₂.

4. A compound as defined by claim 1 wherein R₅ is phenyl.

5. A compound as defined by claim 1 wherein R₅ is

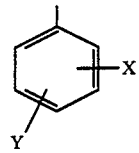

where X and Y are independently hydrogen, fluorine, chlorine, methyl, methoxyl, trifluoromethyl, or nitro, with the proviso that when X is nitro, Y is hydrogen.

6. A compound as defined by claim 1 wherein R₅ is 2-, 3-, or 4-pyridinyl.

7. A compound as defined by claim 1 wherein R₅ is 2- or 3-thienyl, 2- or 3-indanyl, 2- or 3-furanyl, 3- or 4-pyridazinyl, 2-imidazolyl, 2-benzimidazolyl, 2-tetrahydrobenzimidazolyl, 2-perimidyl, or cyclohexyl.

8. A compound as defined by claim 1 having the name N-[(1,1-dimethylethoxy)carbonyl]-α-DL-methyl-tryptophyl-L-phenylalaninamide.

9. A compound as defined by claim 1 having the name N-[(9H-fluoren-9-ylmethoxy carbonyl]-α-methyl-DL-tryptophyl-L-phenylalaninamide.

10. A compound as defined by claim 1 having the name [1-(1H-indole-3-ylmethyl)-1-methyl-2-oxo-2-[(2-phenylethyl)amino]ethyl]carbamic acid, 1,1-dimethylpropyl ester.

11. A compound as defined by claim 1 having the name [2-[[1-(hydroxymethyl)-2-phenylethyl]amino]-1-(1H-indol-3-ylmethyl)-1-methyl-1-oxoethyl]carbamic acid, 1,1-dimethylpropyl ester.

12. A compound as defined by claim 1 having the name (±)-[1-(1H-indol-3-ylmethyl)-1-methyl-2-oxo-2-[[2-(2-pyridinyl)ethyl]amino]ethyl]carbamic acid, 1,1-dimethylpropyl ester.

13. A compound as defined by claim 1 having the name (±)-[1-(1H-indol-3-ylmethyl)-1-methyl-2-oxo-2-[[2-(2-pyridinyl)ethyl]amino]ethyl]carbamic acid, 2,2,2-trichloro-1,1-dimethylethyl ester.

14. A compound as defined by claim 1 having the name (±)-[2-[(2-phenylethyl)amino]-1-(1H-indol-3-ylmethyl)-1-methyl-2-oxoethyl]carbamic acid, 2,2,2-trichloro-1,1-dimethyl ester.

15. A compound as defined by claim 1 having the name (±)-[2-[(2-phenylethyl)amino]-1-(1H-indol-3-ylmethyl)-1-methyl-2-oxoethyl]carbamic acid, 2,2,2-trichloroethyl ester.

16. A compound as defined by claim 1 having the name [1-(1H-indol-3-ylmethyl)-1-methyl-2-oxo-2-[[2-oxo-2-(1-piperidinyl)-1-(phenylmethyl)ethyl]amino]ethyl]carbamic acid, 1,1-dimethylpropyl ester.

17. A compound as defined by claim 1 having the name [2-[[1-(hydroxymethyl)-2-phenylethyl]amino]-1-(1H-indol-3-ylmethyl)-1-methyl-2-oxoethyl]carbamic acid, 2,2,2-trichloro-1,1-dimethylethyl ester.

18. A compound as defined by claim 1 having the name [2-[[1-(hydroxymethyl)-2-phenylethyl]amino]-1-(1H-indol-3-ylmethyl)-1-methyl-2-oxoethyl]carbamic acid, 2,2,2-trichloro-1,1-dimethylethyl ester, pentanedioate salt (2:1).

19. A compound as defined by claim 1 having the name N-[(2,2,2-trichloro-1,1-dimethylethoxy)carbonyl]tryptophylphenylalaninamide.

20. A compound as defined by claim 1 having the name [1-(1H-indol-3-ylmethyl)-1-methyl-2-oxo-2-[[2-(2-pyridinyl)ethyl]amino]ethyl]carbamic acid, 2,2,2-trifluoro-1,1-dimethyl ester.

21. A compound as defined by claim 1 having the name (±)-[1-(1H-indol-3-ylmethyl)-1-methyl-2-oxo-2-[[2-(3-pyridinyl)ethyl]amino]ethyl]carbamic acid, 1,1dimethylpropyl ester.

22. A compound as defined by claim 4 selected from the group consisting of
(±)-α-amino-α-methyl-N-(2-phenylethyl)-1H-indole-3-propanamide;
(±)-[1-(1H-indol-3-ylmethyl)-1-methyl-2-oxo-2-[(2-phenylethyl)amino]ethyl]carbamic acid, 9H-fluoren-9-ylmethyl ester;
(±)-α-[(2,3-dimethyl-1-oxobutyl)amino]-α-methyl-N-(2-phenylethyl)-1H-indole-3-propanamide;
(±)-α-[[[(1,1-dimethylethyl)amino]carbonyl]amino]α-methyl-N-(2-phenylethyl)-1H-indole-3-propanamide;
(R)-[2-[(1,1-dimethyl-2-phenylethyl)amino]-1-(1H-indol-3-ylmethyl)-2-oxoethyl]carbamic acid, 1,1-dimethylpropylester;
(S)-[2-[(1,1-dimethyl-2-phenylethyl)amino]-1-(1H-indol-3-ylmethyl)-2-oxoethyl]carbamic acid, 1,1-dimethylpropylester;
[2-[[1-(hydroxymethyl)-2-phenylethyl]amino]-1-(1H-indol-3-ylmethyl)-1-methyl-2-oxoethyl]carbamic acid, 2,2,2-trichloro-1,1-dimethylethyl ester;
N-[1-(1H-indol-3-ylmethyl)-1-methyl-2-oxo-2-[(4-phenylbutyl)amino]ethyl]carbamic acid, 1,1-dimethylpropyl ester;
N-[(1,1-dimethylpropoxy)carbonyl]-DL-tryptophyl-L-phenylalanine, methyl ester; and
N-[(2,2,2-trichloro-1,1-dimethylethoxy)carbonyl]-L-tryptophyl-Nα-methyl-DL-phenylalaninamide.

23. A compound as defined by claim 5 selected from the group consisting of:
(±)-[1-(1H-indol-3-ylmethyl)-2-[[2-(4-methoxyphenyl)ethyl]amino]-1-methyl-2-oxoethyl]carbamic acid, 1,1-dimethylpropyl ester;
(±)-[2-[[2-(4-chlorophenyl)ethyl]amino]-1-(1H-indol-3-ylmethyl)-1-methyl-2-oxoethyl]carbamic acid, 1,1-dimethylpropyl ester;
(±)-[2-[[2-(3,4-dichlorophenyl)ethyl]amino]-1-(1H-indol-3-ylmethyl)-1-methyl-2-oxoethyl]carbamic acid, 1,1-dimethylpropyl ester 24. A compound as defined by claim 6 selected from the group consisting of
(R)-[1-(1H-indol-3-ylmethyl)-1-methyl-2-oxo-2-[[2-(2-pyridinyl)ethyl]amino]ethyl]carbamic acid, 2,2,2-trichloro-1,1-dimethylethyl ester;
(±)-[1-(1H-indol-3-ylmethyl)-1-[[[2-(2-pyridinyl)ethyl]amino]carbonyl]propyl]carbamic acid, 2,2,2-trichloroethyl ester;
[1-(1H-indol-3-ylmethyl)-1-methyl-2-oxo-2-[[2-(2-pyridinyl)ethyl]amino]ethyl]carbamic acid, 2,2,2-trifluoro-1,1-dimethyl ester;
[1-(1H-indol-3-ylmethyl)-1-methyl-2-oxo-2-[[2-(2-pyridinyl)ethyl]amino]ethyl]carbamic acid, 2,2-difluoro-1-(fluoromethyl)ethyl ester; and
(±)-[1-(1H-indol-3-ylmethyl)-1-methyl-2-oxo-2-[[2-(4-pyridinyl)ethyl]amino]ethyl]carbamic acid, 1,1-dimethylpropyl ester.

25. A compound as defined by claim 7 selected from the group consisting of:
(±)-[2-[(2,3-dihydro-1H-inden-1-yl)amino]-1-(1H-indol-3-ylmethyl)-1-methyl-2-oxoethyl]carbamic acid, 2,2,2-trichloro-1,1-dimethylethyl ester;
(±) [2-[(2,3-dihydro-1H-inden-2-yl)amino]-1-(1H-indol-3-ylmethyl)-1-methyl-2-oxoethyl]carbamic acid, 2,2,2-trichloro-1,1-dimethylethyl ester;
[2-[[2-amino-2-oxo-1-(2-thienylmethyl)ethyl]amino]-1-(1H-indol-3-ylmethyl)-1-methyl-2-oxoethy-1]-carbamic acid, 1,1-dimethylpropyl ester;
(±)-[1-(1H-indol-3-ylmethyl)-1-methyl-2-oxo-2-[(2-thienylethyl)amino]ethyl]carbamic acid, 1,1-dimethylpropyl ester;
(±)-[2-[[2-(2-furanyl)ethyl]amino-1-(1H-indol-3-ylmethyl)-1-methyl-2-oxoethyl]carbamic acid, 1,1-dimethylpropyl ester;
(±)-[1-(1H-indol-3-ylmethyl)-1-methyl-2-oxo-2-[[2-(3-pyridazinyl)ethyl]amino]ethyl]carbamic acid, 1,1-dimethylpropyl ester;
(±)-[2- [[2-(1H-benzimidazol-2-yl)ethyl]ethyl]amino]-(1H-indol-3-ylmethyl)-1-methyl-2-oxoethy-1]-carbamic acid, 1,1-dimethylpropyl ester;
[1-(1H-indol-3-ylmethyl)-1-methyl-2-oxo-2-[[2-(1H-perimidin-2-yl)ethyl]amino]ethyl]carbamic acid, 1,1-dimethylpropyl ester; and
(±)-[2-[(2-cyclohexylethyl)amino]-1-(1H-indol-3-yl)methyl)-1-methyl-2-oxoethyl]carbamic acid, 1,1-dimethylpropyl ester.

26. A pharmaceutical composition comprising an amount of a compound as defined by claim 1 effective to suppress the food intake of a mammal together with a pharmaceutically acceptable carrier.

27. A method of suppressing the food intake of a mammal comprising administering to a mammal in need of such treatment an appetite suppressing effective amount of a pharmaceutical composition as defined by claim 26.

* * * * *